US00PP31503P3

(12) United States Plant Patent
Manly

(10) Patent No.: US PP31,503 P3
(45) Date of Patent: Mar. 3, 2020

(54) APPLE TREE NAMED 'REGAL D5-100'

(50) Latin Name: *Malus domestica*
Varietal Denomination: Regal D5-100

(71) Applicant: Regal Fruit International, LLC, Ephrata, WA (US)

(72) Inventor: Neal Manly, Ephrata, WA (US)

(73) Assignee: Regal Fruit International, LLC, Ephrata, WA (US)

( * ) Notice: Subject to any disclaimer, the term of this patent is extended or adjusted under 35 U.S.C. 154(b) by 0 days.

(21) Appl. No.: 15/998,131

(22) Filed: Jul. 6, 2018

(65) Prior Publication Data

US 2020/0015399 P1 Jan. 9, 2020

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

*Primary Examiner* — Kent L Bell
(74) *Attorney, Agent, or Firm* — Lee & Hayes, P.C.

(57) ABSTRACT

A new and distinctive variety of *Malus domestica* apple from a controlled cross of Huaguan x Honeycrisp that is distinctly different from its parents.

6 Drawing Sheets

Latin name: *Malus domestica.*
Varietal denomination: 'Regal D5-100'.

BACKGROUND

The present invention relates to a new, novel, and distinct variety of apple tree, and which has been denominated varietally as 'Regal D5-100,' and more specifically, to a novel apple tree with an upright growth habit with moderate vigor that may be pollinated from any other diploid apple of a mid-season bloom. The novel apple tree also produces fruit that are medium in size and that have streaked bi-color, that are slightly lopsided, and that exhibit four months of common storage life.

ORIGIN AND ASEXUAL REPRODUCTION

It has long been recognized that an important factor contributing to the success of a new variety of apple tree bearing fresh market fruit is its growing characteristics as well as characteristics of its fruit. Additionally, another significant factor affecting the commercial viability of a new variety of apple relates to its storage characteristics, and which are reflected by such pomological traits as fruit pressure, soluble solids, and pH to name but a few. The new variety of apple tree described herein was derived by the following methodology. The new variety 'Regal D5-100' was derived by a controlled pollination of the variety Huaguan (U.S. Plant Pat. No. 11,077) with the pollen from Honeycrisp (U.S. Plant Pat. No. 7,197) in spring 2007. Seeds from this cross were collected in the spring of 2008. Resulting seedling wood was budded onto NIC 29 rootstock in 2009. In 2011, these trees were planted in a research plot located near 3560 RD 5 NW, Ephrata, Wash. 98823. In 2013, 'Regal D5-100' was selected. Second generation trees were budded on NIC 29 in the spring of 2014 and planted in the spring of 2015 at 22064 RD 6 NW, Quincy Wash. 98848. Fruit generated from the second-generation trees have been studied and compared and it appears that all characteristics of the subsequent asexually reproductive trees remain true to that seen in the original first generation tree.

SUMMARY OF NEW VARIETY

The 'Regal D5-100' apple tree is characterized as to novelty by its distinctive traits from its parent varieties, Huaguan and Honeycrip. By way of example, 'Regal D5-100' exhibits semi-spur characteristics, exhibits upright growth habit with moderate vigor as grown on NIC 29 rootstock, is a mid-season bloomer and will allow for pollination from any other diploid apple of the same bloom season. 'Regal D5-100' has a tendency to exhibit alternate bearing following a heavy crop load. Fruit at maturity is medium in size, has a streaked bi-color and is slightly lopsided. The fruit exhibits four months of common storage life. The fruit is further sensitive to bruising and does not exhibit bitterpit. 'Regal D5-100' is susceptible to powdery mildew and is moderately susceptible to fireblight.

BRIEF DESCRIPTION OF DRAWINGS

The accompanying drawings are color photographs of the present variety.

FIG. 6 illustrates a comparison of mature fruit indices of 'Regal D5-100', Huaguan, and Honeycrisp.

NOT A COMMERCIAL WARRANTY

Figure 1:
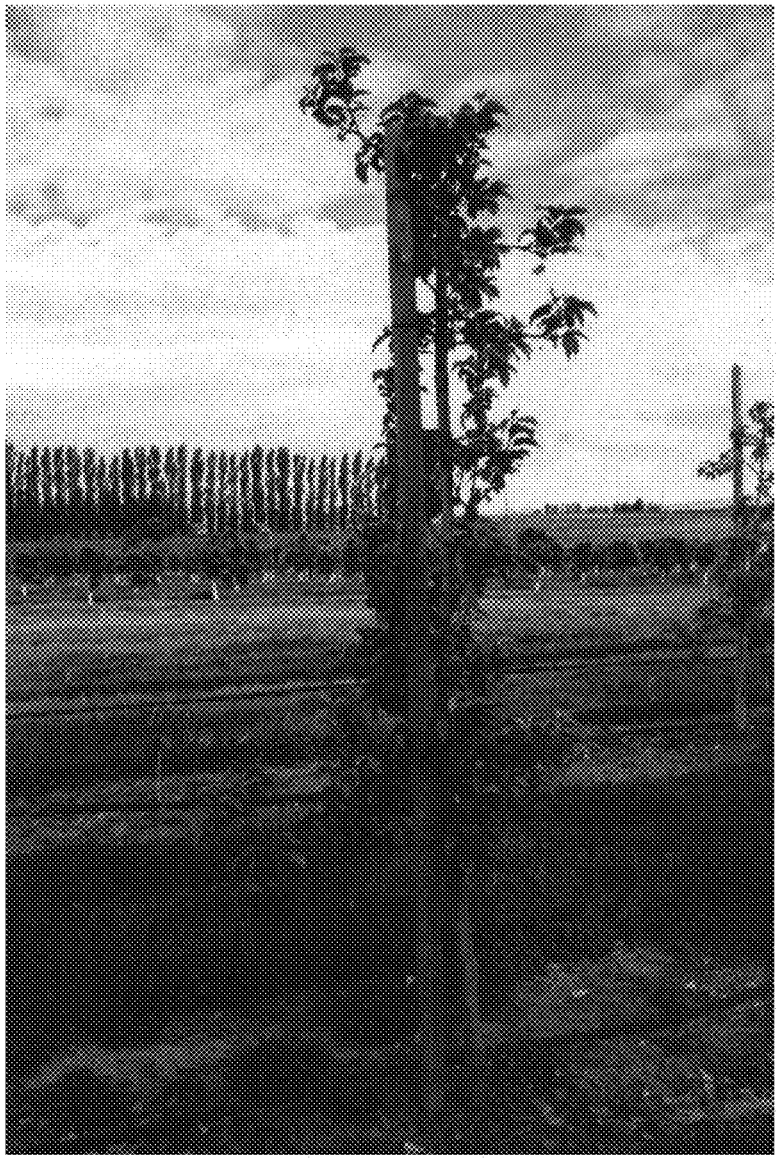
FIG. 1 depicts a 'Regal D5-100' tree at full bloom stage.
Figure 2:
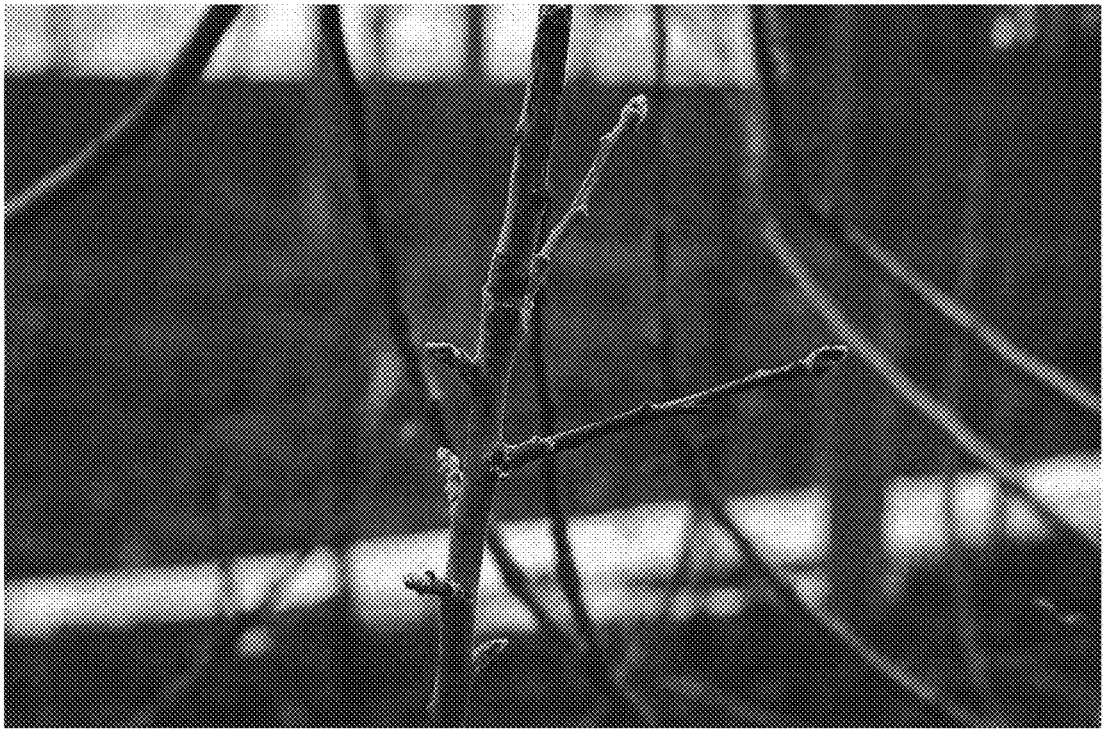
FIG. 2 depicts 'Regal D5-100' spur development.
Figure 3:
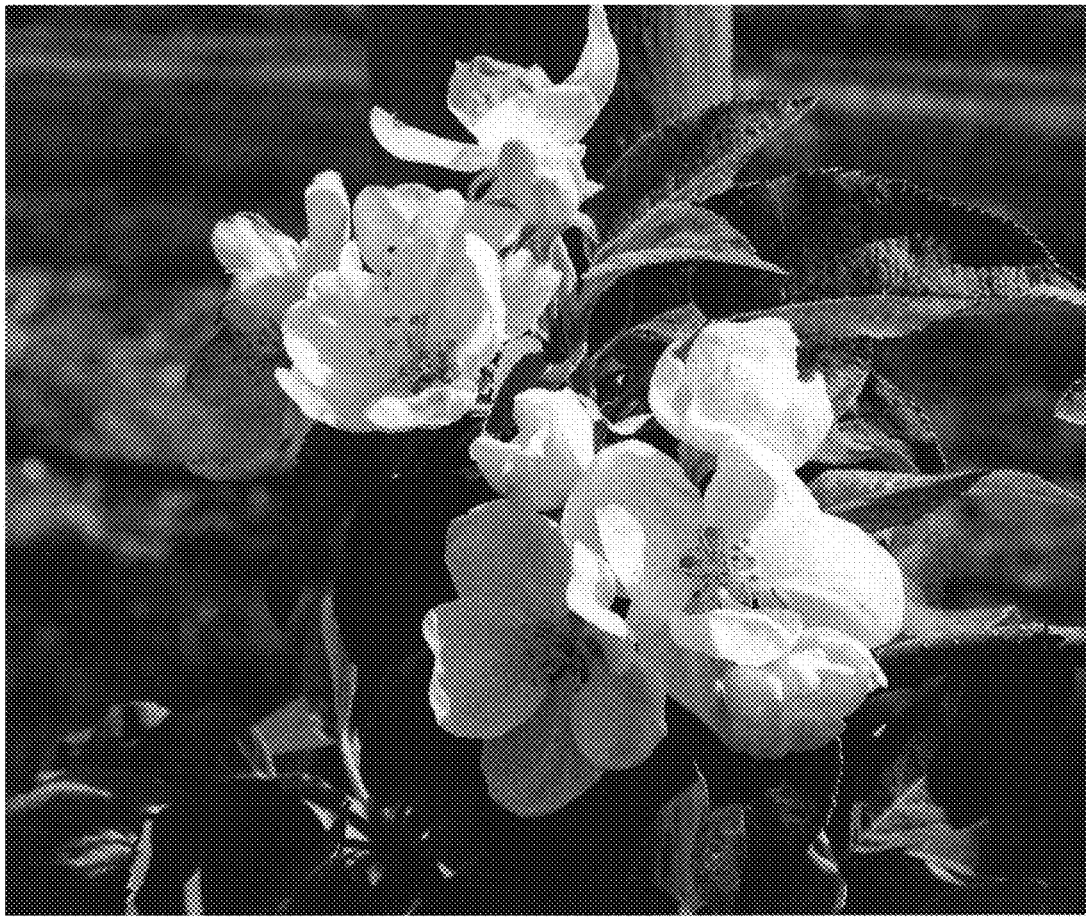
FIG. 3 depicts a typical blossom cluster of 'Regal D5-100' at full bloom.
Figure 4:
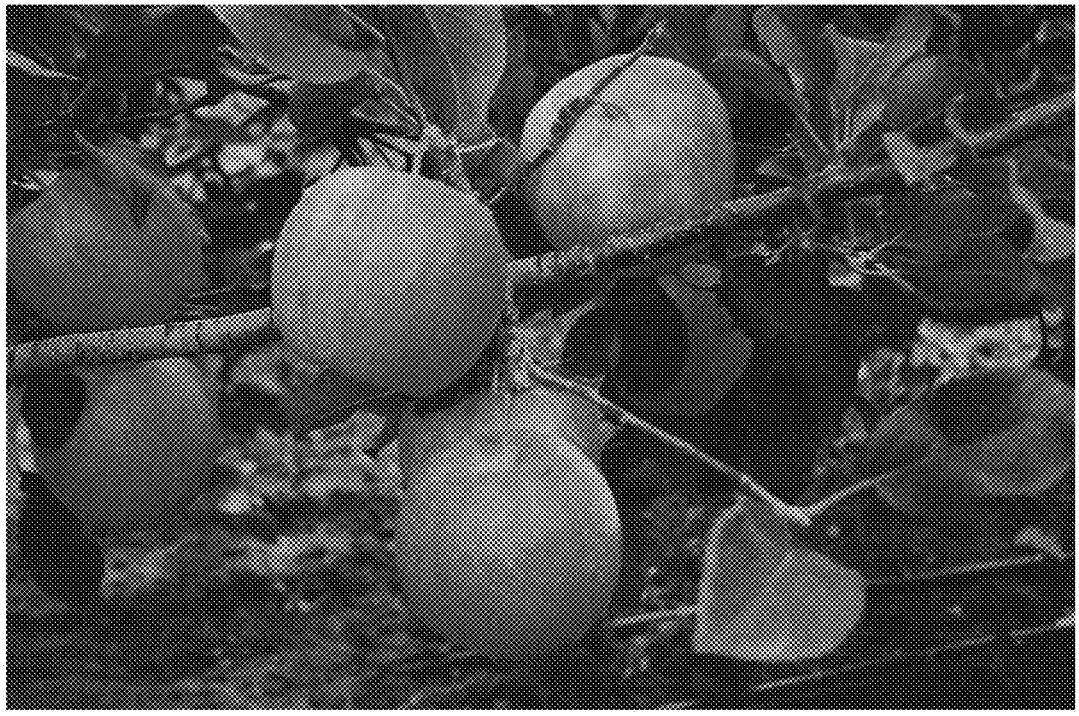
FIG. 4 depicts a fruiting limb of 'Regal D5-100' at harvest maturity.
Figure 5:
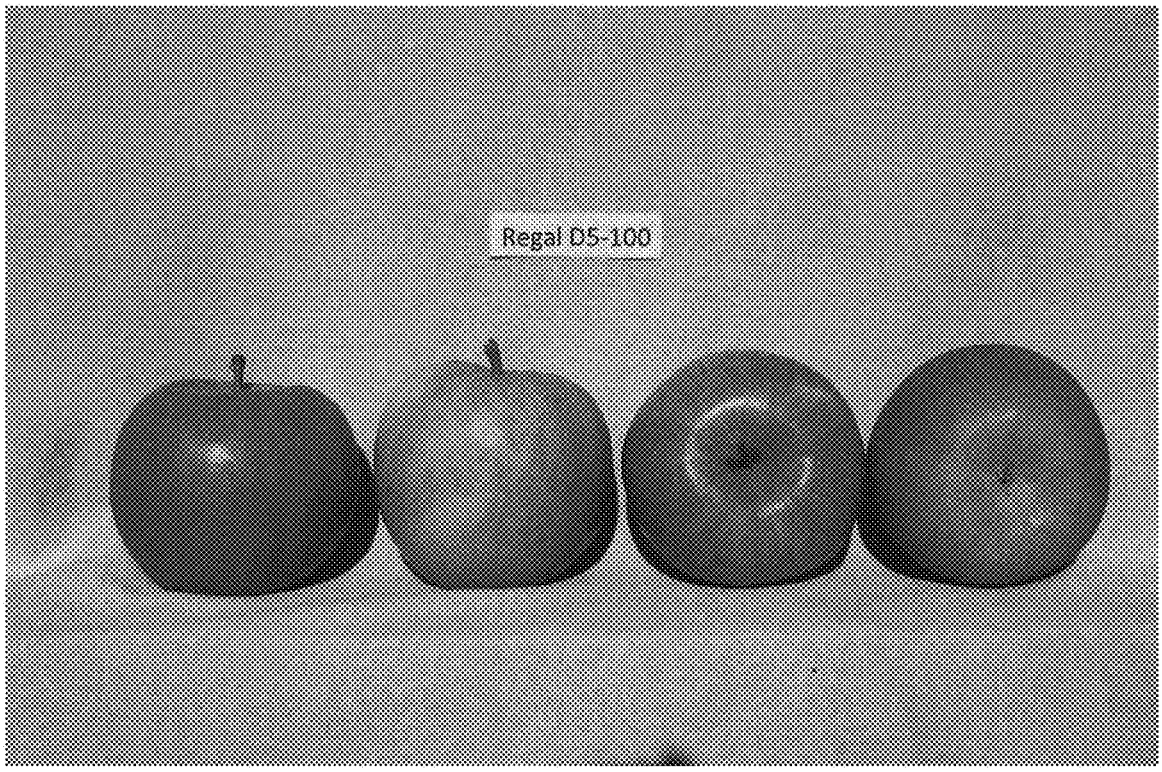
FIG. 5 illustrates four positions of harvest-mature 'Regal D5-100' fruit.

The following detailed description has been prepared to solely comply with the provisions of 35 U.S.C. § 112, and does not constitute a commercial warranty, (either expressed or implied), that the present variety will, in the future, display the botanical, pomological or other characteristics as set forth herein. Therefore, this disclosure may not be relied upon to support any future legal claims, including but not limited to breach of warranty of merchantability, or fitness for any particular purpose, which is directed, in whole, or in part, to the present variety.

DETAILED DESCRIPTION

Referring more specifically to the pomological and botanical details of this new and distinct variety of apple tree, the following has been observed during the 2016 and 2017 growing season under the ecological conditions prevailing in a test orchard which is located near Quincy, Wash. All major color code designations are by reference to The RHS Colour Chart provided by The Royal Horticultural Society of Great Britain.

The parents of the 'Regal D5-100' are the Honeycrisp tree and the Huaguan tree. The following are some of the characteristics that distinguish the 'Regal D5-100' from its parents. The 'Regal D5-100' leaf length falls in between the length of the Honeycrisp and the Huaguan. The 'Regal D5-100' is more oblong in nature with a wider base and tapers at the top. Honeycrisp is more oval in nature. Huaguan is a more slender and smaller leaf than the Honeycrisp and the 'Regal D5-100.' The 'Regal D5-100' has more "teeth" on the serrated edge whereas Honeycrisp's are fewer and more rounded in nature. Huaguan's "teeth" are finer and less rounded than the Honeycrisp and the 'Regal D5-100.' Huaguan's younger leaves on the terminal have a much more yellowish hue than either the Honeycrisp or the 'Regal D5-100.' The Honeycrisp has finer (thinner) wood in its branching when compared to both the Huaguan and the 'Regal D5-100.' The 'Regal D5-100' appears to be more upright in its growth characteristics than both the Honeycrisp and the Huaguan. Both the 'Regal D5-100' and the Huaguan are much more vigorous than the Honeycrisp. The Honeycrisp is a very weak grower, whereas the 'Regal D5-100' and Huaguan have vigor similar to that of a Fuji tree.

The closest cultivar to the 'Regal D5-100' is the Huaguan tree. The following are some characteristics to distinguish the 'Regal D5-100' from its closest cultivar, the Huaguan. The 'Regal D5-100' leaf length longer than the Huaguan. The 'Regal D5-100' is more oblong in nature with a wider base and tapers at the top. Huaguan is a more slender and smaller leaf that the 'Regal D5-100.' The Huaguan's "teeth" are finer and less rounded than the 'Regal D5-100.' Huaguan's younger leaves on the terminal have a much more yellowish hue than the 'Regal D5-100.' The 'Regal D5-100' appears to be more upright in its growth characteristics than the Huaguan.

TREE

Tree type: The present variety is a central leader as trained to wire.
Tree vigor: Considered moderate.
Tree shape: Inverted narrow cone.
Tree height: The present variety, when measured during its ninth leaf, has an overall height of about nine feet.
Tree width: As measured during the ninth leaf, the new tree exhibits a width of about three feet.
Hardiness: Considered hardy for the current region where it is being grown.
Fruit productivity: Considered moderately high for the species.
Bushel production: About 1.25 bushels per tree.

TRUNK

Trunk size: The tree diameter is about 5.4 centimeters when measured at a height of about 30 centimeters above the ground.
Bark texture: Smooth.
Bark color: Generally Greyed-Orange (RHS N167A).
Trunk lenticels: Generally present, moderate in number, and averaging about nine lenticels in a four-centimeter square area.
Trunk lenticel width: About 1.5 millimeters to about 1.7 millimeters with an average of 1.6 millimeters.
Trunk lenticel length: About 2.3 millimeters to about 3.6 millimeters with an average of about 3.2 millimeters.
Trunk lenticel color: Generally on the outer margin from the greyed-white group (RHS 156A) and on the center from the black-group (RHS 202A).
Trunk lenticel shape: Generally flat rectangular.

BRANCHES

First-year-branches:
First-year branch diameter: About 1.2 centimeters to about 2.1 centimeters with an average of 1.8 centimeters as measured at 10 centimeters from trunk.
First-year branch color: Greyed-Orange (RHS N176A).
First-year branch shape: Generally scaffold branches.
First-year branch texture: Generally smooth.
First-year branch lenticels: Numbers—Averaging about 17 per running centimeter of growth.
First-year branch lenticel shape: Generally flat rectangular.
First-year branch lenticel length: Generally from about 2.2 millimeters to about 5.8 millimeters with an average of about 3.6 millimeters.
First-year branch lenticel width: Generally from about 1.3 millimeters to about 1.7 millimeters with an average of about 1.5 millimeters.
First-year branch lenticel color: Generally from the Greyed-White group (RHS 156A).
Two-year-old fruiting branches:
Two-year-old branch diameter: When measured at the midpoint of growth of about 5.6 millimeters to about 6.5 millimeters with an average of about 5.9 millimeters.
Two-year-old branch color: Greyed-Orange (RHS 165B).
Two-year-old branch lenticel numbers: Averaging about 17 lenticels per square centimeter of surface area.
Two-year-old branch lenticel shape: Generally round.
Two-year-old branch lenticel diameter: From about 0.8 millimeters to about 1.2 millimeters.
Two-year-old branch lenticel color: Greyed-White (RHS 156C).
Two-year-old branch spur development: Considered semi-spur type.
Two-year-old branch spur length: About 7.4 millimeters to about 10.6 millimeters with an average of about 9.0 millimeters.
Two-year-old branch bud shape: Generally Acute.
Two-year-old branch spur bud length: About 7.4 millimeters to about 10.6 millimeters with an average of 9.0 millimeters.

Two-year-old branch tip bud length: About 7.4 millimeters to about 10.6 millimeters with an average of 9.0 millimeters.

Two-year-old branch spur width: About 3.9 millimeters to about 5.0 millimeters with an average of about 4.5 millimeters.

Two-year-old branch spur bud diameter: About 3.9 millimeters to about 5.0 millimeters with an average of about 4.5 millimeters.

Two-year-old branch bud scale color: Greyed-Purple (RHS 187A).

Two-year-old branch spur pubescence: Moderately heavy over about 90-100% of surface.

Two-year-old branch spur pubescence color: Greyed-White (RHS 156D).

Two-year-old branch crotch angle: About 60 degrees to about 75 degrees, otherwise described as about 60 percent to about 75 percent.

2018 branches:

2018 branch texture: Generally smooth.

2018 branch length: About 23 centimeters to about 54 centimeters with an average of about 36.6 centimeters.

2018 branch diameter at midpoint: About 4.8 millimeters to about 6.5 millimeters with an average of about 5.8 millimeters.

2018 branch pubescence: Present and light over 20-40% of surface area.

2018 branch pubescence color: Greyed-White group 156D.

2018 branch color: Greyed-Orange (RHS 166A).

2018 branch lenticels: Present and averaging about 19 per running centimeter of branch.

2018 branch lenticel shape: Generally round.

2018 branch lenticel diameter: About 0.5 millimeters to about 0.8 millimeters with an average of about 0.6 millimeters.

2018 branch lenticel color: Greyed-White (RHS 156D).

2018 branch internode length: About 18.3 millimeters to about 36.4 millimeters with an average of about 28.9 millimeters.

BLOOM (FLOWERS)

Number blossoms per cluster: From about 4 to 6, mostly 5.

Size: Generally considered medium-large to large.

Diameter when fully open: From about 42 millimeters to about 48 millimeters with an average of about 45 millimeters.

Petal count: 5.

Petal shape: Generally oval, most tips round with about 25% being obcordate.

Petal width: From about 13.6 millimeters to about 20.2 millimeters with an average of about 17.7 millimeters.

Petal length: From about 19.8 millimeters to about 23.4 millimeters with an average of about 21.4 millimeters.

Petal depth: From about 4.0 millimeters to about 7.0 millimeters with an average of about 4.7 millimeters.

Petal color: White Group (RHS N155D). About 20-80% of the undersurface from Red-Purple Group (RHS N66D). Veins in blushed areas from Red-Purple Group (RHS N66A).

Petal margin: Smooth.

Petal base: Round.

Stamen number: 20.

Stamen filament length: From about 6.0 millimeters to about 8.2 millimeters with an average of about 6.9 millimeters.

Stamen filament color: White Group (RHS 155C).

Stamen anthers shape: Generally Kidney.

Stamen anthers width: From about 1.5 millimeters to about 2.0 millimeters with an average of about 1.8 millimeters.

Stamen anthers length: From about 2.0 millimeters to about 2.8 millimeters with an average of about 2.4 millimeters.

Stamen anthers color: Yellow-Orange Group (RHS 18C).

Stamen anthers pollen: Generally moderate in density.

Stamen anthers pollen color: Greyed-Orange Group (RHS 165B).

Pistil length: From about 10.1 millimeters to about 13.2 millimeters with an average of about 11.4 millimeters. Splits into five branches at an average of about 3.4 millimeters from base.

Pistil color: Yellow-Green Group (RHS 145A).

Pubescence: Generally small, lite density patches at the fused area. Color is from the While Group (RHS 155C).

Stigma number: 5.

Stigma shape: Generally Club.

Stigma color: Yellow-Orange Group (RHS 20A).

Sepal number: 5.

Sepal shape: Generally Lanceolate.

Sepal shape at tip: Acuminate.

Sepal shape at base: Truncate.

Sepal length: From about 7.4 millimeters to about 11.7 millimeters with an average of about 9.6 millimeters.

Sepal width: From about 2.9 millimeters to about 4.8 millimeters with an average of about 3.9 millimeters.

Sepal color: Yellow-Green Group (RHS 146B). Tips highlighted from the Greyed-Orange Group (RHS 172A).

Sepal margin: Smooth.

Sepal pubescence: Moderately heavy over 100% of surfaces. Color from White Group (RHS 155C).

Peduncle length: From about 23.0 millimeters to about 32.7 millimeters with an average of about 29.2 millimeters.

Peduncle diameter at midpoint: From about 1.3 millimeters to about 1.6 millimeters with an average of about 1.5 millimeters.

Peduncle color: Yellow-Green Group (RHS 144A).

Peduncle pubescence: Moderate in density over 100% surface area.

Peduncle pubescence color: White Group (RHS 155C).

Thalmus depth: From about 4.0 millimeters to about 7.0 millimeters with an average of about 4.7 millimeters.

Thalmus color: Yellow-Green Group (RHS 147A).

Thalmus pubescence: Abundant and tenacious over about 100% of surface area. Color from White Group (RHS 155C).

BLOOM PERIOD

First bloom: From about April $13^{th}$ to about May $11^{th}$ with an average of about April $27^{th}$.

Full bloom: From about April $16^{th}$ to about May $14^{th}$ with an average of about April $30^{th}$.

FLOWER BUDS

Shape: Generally acute.

Length: About 7.4 millimeters to about 10.6 millimeters with an average of about 9.0 millimeters.

Diameter: About 3.9 millimeters to about 5.0 millimeters with an average of about 4.5 millimeters.
Color: Greyed-Purple (RHS 187A).

LEAVES

Shape: Generally oval and upward lifting.
Upper texture: Generally leathery and smooth with sunken veins.
Lower texture: Generally smooth with raised veins.
Upper sheen: Generally high.
Lower sheen: Generally dull.
Pubescence: Light density on about 100% of lower surface only.
Pubescence color: White Group (RHS 155B).
Length: From about 6.9 centimeters to about 8.8 centimeters with an average of about 8.0 centimeters.
Width: From about 4.5 centimeters to about 6.0 centimeters with an average of about 5.2 centimeters.
Margin: Generally serrulate.
Tip: Generally acuminate.
Base: Generally rounded.
Upper blade color: Green Group (RHS 137A).
Lower blade color: Yellow-Green Group (RHS 146B).
Stipules: Present and two on leaves.
Stipules shape: Subulate.
Stipules length: From about 14.9 millimeters to about 21.6 millimeters with an average of about 17.4 millimeters.
Stipules width: From about 1.6 millimeters to about 2.4 millimeters with an average of about 2.1 millimeters.
Stipules color: Green Group (RHS 137A).
Stipules pubescence: Generally very light density covering about 100% of lower surface.
Stipules pubescence color: White Group (RHS 155B).
Stipules mid vein: Generally prominent on blade lower surface.
Stipules mid vein width at midpoint: From about 1.1 millimeters to about 1.9 millimeters with an average of about 1.5 millimeters.
Stipules mid vein color: Yellow-Green Group (RHS 145C).
Stipules mid vein pubescence: Generally light density covering about 100% of prominent undersurface.
Stipules mid vein pubescence color: White Group (RHS 155B).
Petiole: Generally has a shallow groove running the length of the upper surface.
Petiole length: From about 27.5 millimeters to about 32.2 millimeters with an average of about 29.4 millimeters.
Petiole diameter at midpoint: From about 1.4 millimeters to about 1.9 millimeters with an average of about 1.6 millimeters.
Petiole color: Greyed-Green Group (RHS 194B) with the basal end highlighted from Greyed-Purple Group (RHS 185C).
Petiole pubescence: Moderate in density over entire surface.
Petiole pubescence color: White Group (RHS 155B).

FRUIT

Individual weight: About 0.455 pounds (206 grams) to about 0.500 pounds (227 grams).
Generally: The observations which follow have been taken from the first-generation tree fruit.
Form: Considered oblate in shape, regular at equatorial axis, and mildly lopsided.
Equatorial diameter: From about 7.3 millimeters to about 7.9 millimeters with an average of about 7.6 millimeters.
Axis diameter: From about 6.4 millimeters to about 7.5 millimeters with an average of about 6.9 millimeters.
Stem: Generally variable in length from medium to long, with mostly long stem that is not clubbed.
Stem length: From about 13.3 millimeters to about 36.2 millimeters with an average of about 27.2 millimeters.
Stem diameter: From about 2.2 millimeters to about 3.3 millimeters with an average of about 2.7 millimeters.
Stem color: Outer two-thirds from the Greyed-Purple Group (RHS 183D). Remaining one-third cavity end from the Greyed-Green Group (RHS 194B).
Stem pubescence: Present covering about 100% and light to medium in density.
Stem pubescence color: Green-White Group (RHS 157C).
Stem cavity shape: Generally cone shaped and acute.
Stem cavity lipped: No.
Stem cavity russet: Generally lite to moderate in density.
Stem cavity russet color: Greyed-Orange Group (RHS 163B).
Stem cavity width: From about 29.1 millimeters to about 37.7 millimeters with an average of about 36.8 millimeters.
Stem cavity depth: From about 12.8 millimeters to about 20.2 millimeters with an average of about 16.2 millimeters.
Basin cavity ribbed: Yes.
Basin cavity sides: Considered sloping.
Basin cavity width: From about 27.4 millimeters to about 33.6 millimeters with an average of about 30.4 millimeters.
Basin cavity depth: From about 9.4 millimeters to about 13.6 millimeters with an average of about 11.1 millimeters.
Basin cavity eye: Closed and erect with relaxed tips. Sepal color from the Yellow-Green Group (RHS 152A).
Basin cavity eye pubescence: Moderate density over about 100% of upper and lower surfaces.
Basin cavity eye pubescence color: Green-White Group (RHS 157B).
Skin appearance: Generally streaked over about 90% of the surface and is hammered with scant bloom.
Skin color: Generally streaks from the Red Group (RHS 45A), streaked background from the Orange-Red Group (RHS 34A), non-streaked background from the Green-Yellow Group (RHS 1C).
Skin thickness: Considered thin.
Skin texture: Generally brittle and tender.
Skin lenticels: Present, prominent, and distributed uniformly.
Skin lenticels shape: Generally round ranging from about 0.7 millimeters to about 0.8 millimeters.
Skin lenticels number: 10 per square centimeter.
Skin lenticels color: White Group (RHS N155D).
Core position: Considered distant from stalk.
Core line position: Considered basal.
Core shape: Generally flat and round.
Core length: From about 21.3 millimeters to about 27.5 millimeters with an average of about 24.9 millimeters.
Core diameter: From about 26.6 millimeters to about 40.2 millimeters with an average of about 35.2 millimeters.
Cell tufted: No.
Cell shape: Lanceolate.
Cell length: From about 14.1 millimeters to about 18 millimeters with an average of about 16.9 millimeters.

Cell width: From about 10 millimeters to about 13.9 millimeters with an average of about 12.0 millimeters.

Cell wall-to-wall distance: From about 5.2 millimeters to about 6.9 millimeters with an average of about 5.8 millimeters.

Tube shape: Funnel.

Tube stamen position: Considered median.

Tube axis: closed.

Seed mumber: 1-3, Mostly 2.

Seed shape: Acute.

Seed length: From about 8.7 millimeters to about 10 millimeters with an average of about 9.2 millimeters.

Seed width: From about 4.5 millimeters to about 5.7 millimeters with an average of about 5.2 millimeters.

Seed depth (side to side): From about 3.0 millimeters to about 3.6 millimeters with an average of about 3.3 millimeters.

Seed color: Greyed-Purple Group (RHS 187A).

Flesh: Juicy, crisp and breaking, melting and moderately sub-acid.

Flesh color: Yellow-White Group (RHS 158A).

Aroma: Mostly wanting with occasional mild apple like.

Date of harvest maturity: Oct. 10, 2017.

Maturity pressure: 16.9#.

Maturity starch: 3.5.

Maturity soluble solids: 12.4.

Keeping quality: Very good. Up to 4 months in common storage.

Productivity: On rootstock grown will produce approximately 1 bushel per tree.

Pollination: Any diploid apple of the same bloom season.

Use: Desert. Excellent eating quality that is snappy, juicy, sweet with very good acid balance and melting skin.

Disease and insect resistance: Considered to be susceptible to all insects and diseases found in the region of Central Washington. Fruit does not exhibit any physiological disorders on the tree nor during storage for the duration of normal storage lengths. 'Regal D5-100' has undergone virus screen in 2017 and found to be free of the 12 viruses.

Although the new variety of apple tree possesses the described characteristics when grown under the ecological conditions prevailing in Quincy, Wash., in the south-central part of Washington state, it should be understood that variations of the usual magnitude and characteristics incident to changes in growing conditions, fertilization, pruning and pest control as well as horticultural management practices are to be expected.

What is claimed is:

1. A new and distinct variety Apple tree named 'Regal D5-100' as herein illustrated and described.

* * * * *

| Variety | Harvest Date | Run Date | Pressure | Brix | pH | Acid* |
|---|---|---|---|---|---|---|
| Regal D5-100 1st gen. | 10/10/2017 | 10/11/2017 | 16.2 | 12.6 | 3.3 | 7.79 |
| Regal D5-100 2nd gen | 10/10/2017 | 10/11/2017 | 16.9 | 12.4 | 3.36 | 8.00 |
| Huaguan | 10/11/2017 | 10/11/2017 | 15.7 | 11.9 | 3.73 | 5.78 |
| Honeycrisp | 9/15/2017 | 9/18/2017 | 15.8 | 12.2 | 3.4 | 7.5 |

* measured as g/L using 0.1M NaOH.

FIG. 6